US008801602B2

(12) United States Patent  
Sekiguchi et al.

(10) Patent No.: US 8,801,602 B2
(45) Date of Patent: Aug. 12, 2014

(54) ENDOSCOPE INSERTION SHAPE OBSERVATION PROBE

(71) Applicant: Olympus Medical Systems Corp., Tokyo (JP)

(72) Inventors: Masahiko Sekiguchi, Akiruno (JP); Masami Fukuchi, Hachioji (JP); Fumiyuki Onoda, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/049,510

(22) Filed: Oct. 9, 2013

(65) Prior Publication Data

US 2014/0039258 A1    Feb. 6, 2014

Related U.S. Application Data

(63) Continuation of application No. PCT/JP2012/073177, filed on Sep. 11, 2012.

(30) Foreign Application Priority Data

Sep. 15, 2011    (JP) ................. 2011-202148

(51) Int. Cl.
*A61B 1/00*     (2006.01)
*A61B 5/06*     (2006.01)
*A61B 1/06*     (2006.01)
*A61B 1/015*    (2006.01)

(52) U.S. Cl.
CPC ............. *A61B 1/00002* (2013.01); *A61B 5/062* (2013.01); *A61B 1/00071* (2013.01); *A61B 1/0669* (2013.01); *A61B 1/00158* (2013.01); *A61B 1/015* (2013.01)
USPC ........................... 600/117; 600/145; 600/424

(58) Field of Classification Search
CPC ...... A61B 1/00; A61B 1/00018; A61B 1/005; A61B 5/06; A61B 5/065
USPC ...................... 600/117, 145, 424; 324/207.16
See application file for complete search history.

(56) References Cited

U.S. PATENT DOCUMENTS 5,840,024 A    11/1998   Taniguchi et al.
5,997,473 A    12/1999   Taniguchi et al.
(Continued)

FOREIGN PATENT DOCUMENTS

JP    07-111969 A    5/1995
JP    10-075929 A    3/1998
(Continued)

OTHER PUBLICATIONS

International Search Report dated Oct. 23, 2012 issued in PCT/JP2012/073177.

*Primary Examiner* — John P Leubecker
(74) *Attorney, Agent, or Firm* — Scully, Scott, Murphy & Presser, P.C.

(57) ABSTRACT

An endoscope insertion shape observation probe including: a bobbin including a first insulation member provided at a front end of a core made of a magnetic member and a second insulation member provided at a rear end of the core; a coil portion formed by winding metal lines on the core; at least two terminal portions to which the metal lines are electrically connected; and signal lines having wires electrically connected to the terminal portions and extended rearward while being sandwiched between an inner circumferential surface of a tube and an outer circumferential portion of the coil portion, wherein the two terminal portions has the wires brazed respectively on surface sides thereof, the surface sides being directed in opposite directions away from each other toward outward of each magnetic coil unit, which improves resistance property of signal lines connected to plural magnetic coil units without increasing an outer diameter.

7 Claims, 7 Drawing Sheets

(56) References Cited

U.S. PATENT DOCUMENTS

| | | | |
|---|---|---|---|
| 6,059,718 A * | 5/2000 | Taniguchi et al. | 600/117 |
| 6,572,535 B2 * | 6/2003 | Watanabe et al. | 600/117 |
| 6,689,049 B1 * | 2/2004 | Miyagi et al. | 600/117 |
| 6,745,065 B2 * | 6/2004 | Niwa et al. | 600/424 |
| 7,648,458 B2 * | 1/2010 | Niwa et al. | 600/130 |
| 7,850,605 B2 * | 12/2010 | Niwa et al. | 600/145 |
| 7,935,047 B2 * | 5/2011 | Yoshida et al. | 600/117 |
| 2002/0128537 A1 * | 9/2002 | Watanabe et al. | 600/117 |
| 2003/0028096 A1 * | 2/2003 | Niwa et al. | 600/424 |
| 2003/0195388 A1 * | 10/2003 | Niwa et al. | 600/117 |
| 2005/0070790 A1 * | 3/2005 | Niwa et al. | 600/424 |
| 2007/0043260 A1 * | 2/2007 | Niwa et al. | 600/117 |
| 2007/0049797 A1 * | 3/2007 | Yoshida et al. | 600/117 |
| 2009/0289621 A1 * | 11/2009 | Petersen | 324/207.16 |
| 2011/0121935 A1 * | 5/2011 | Chu et al. | 336/221 |
| 2013/0102892 A1 * | 4/2013 | Strommer et al. | 600/424 |

FOREIGN PATENT DOCUMENTS

| | | |
|---|---|---|
| JP | 2002-263056 A | 9/2002 |
| JP | 2002-345727 A | 12/2002 |
| JP | 2002-345732 A | 12/2002 |
| JP | 2003-047586 A | 2/2003 |
| JP | 2003-052611 A | 2/2003 |
| JP | 2003-079566 A | 3/2003 |
| JP | 2005-296257 A | 10/2005 |
| JP | 2006-325876 A | 12/2006 |
| JP | 2007-142151 A | 6/2007 |
| JP | 2008-093454 A | 4/2008 |
| WO | WO 2005/096914 A1 | 10/2005 |

* cited by examiner

ENDOSCOPE INSERTION SHAPE OBSERVATION PROBE

CROSS REFERENCE TO RELATED APPLICATION

This application is a continuation application of PCT/JP2012/073177 filed on Sep. 11, 2012 and claims benefit of Japanese Application No. 2011-202148 filed in Japan on Sep. 15, 2011, the entire contents of which are incorporated herein by this reference.

BACKGROUND OF THE INVENTION

1. Field of the Invention

The present invention relates to an endoscope insertion shape observation probe that generates magnetism to be received by an endoscope insertion shape observation apparatus which captures an insertion state of an insertion portion.

2. Description of the Related Art

In a recent colonoscopy which requires advanced technique, an endoscope insertion shape observation apparatus (UPD/Endoscope Position Detecting Unit) that three-dimensionally displays an insertion shape of an insertion portion of an endoscope on a monitor using a magnetic field is known. The UPD does not expose patients to radiation, in contrast to the method of checking an insertion shape using the conventional X-ray photography, and therefore, the examination using the UPD is known as a more effective examination for patients.

When the UPD is used, it is necessary to use an endoscope including, in an insertion portion thereof, a probe incorporating a plurality of magnetic coils, or to insert a dedicated probe having a plurality of magnetic coils in a treatment instrument channel of the endoscope. The magnetism transmitted from the plurality of magnetic coils is received by an antenna arranged at the center of a UPD main body. The UPD connects the positions of the respective magnetic coils obtained by three-dimensionally capturing the received positions of the coils, with a smooth curve, and further performs graphics processing so as to make it easier to view the shape of the insertion portion to display the insertion portion on the monitor.

Regarding the magnetic coil used in such a UPD, for example, Japanese Patent Application Laid-Open Publication No. 7-111969 discloses a technique for covering a part of a connection copper wire connected to a copper wire of the coil with an insulation material and forming an outer surface of the insulation material to be a curved surface, thereby preventing mutual breakage of the internal components of an endoscope and the coil due to interference therebetween caused by bending operation, insertion operation, etc. Regarding the conventional coil, a technique for disposing the coil with the direction thereof reversed is disclosed, in order to improve the bending resistance of the coil, when the coil is incorporated into an endoscope.

In addition, for example, Japanese Patent Application Laid-Open Publication No. 2007-142151 discloses a technique for reducing the size of the coil device and improving assembly thereof by integrally forming an external connection terminal at an end portion of an iron core on which the coil is wound.

SUMMARY OF THE INVENTION

An endoscope insertion shape observation probe according to one aspect of the present invention is an endoscope insertion shape observation probe including a plurality of magnetic coil units disposed in a tube, and includes: a bobbin including a first insulation member provided at a front end of a core made of a magnetic member and a second insulation member provided at a rear end of the core; a coil portion formed by winding metal lines on the core; at least two terminal portions to which the metal lines are electrically connected; and signal lines, wires of which are electrically connected to the terminal portions, the signal lines being extended rearward while being sandwiched between an inner circumferential surface of the tube and an outer circumferential portion of the coil portion, wherein the at least two terminal portions are formed such that the wires are brazed respectively on surface sides of the respective terminal portions, the surface sides being directed in opposite directions away from each other toward outward of each of the plurality of magnetic coil units.

DETAILED DESCRIPTION OF THE PREFERRED EMBODIMENT

Hereinafter, description will be made on an endoscope insertion shape observation probe according to the present invention. Note that each of the drawings based on each embodiment is a pattern diagram, and care should be taken to the fact that the relationship between the thicknesses and widths of the respective members, a ratio of the thickness of a certain member to that of another member, and the like are different from the actual sizes, and there is a case where the respective drawings include parts in which the relationships and ratios among the dimensions are different.

Figure 1:
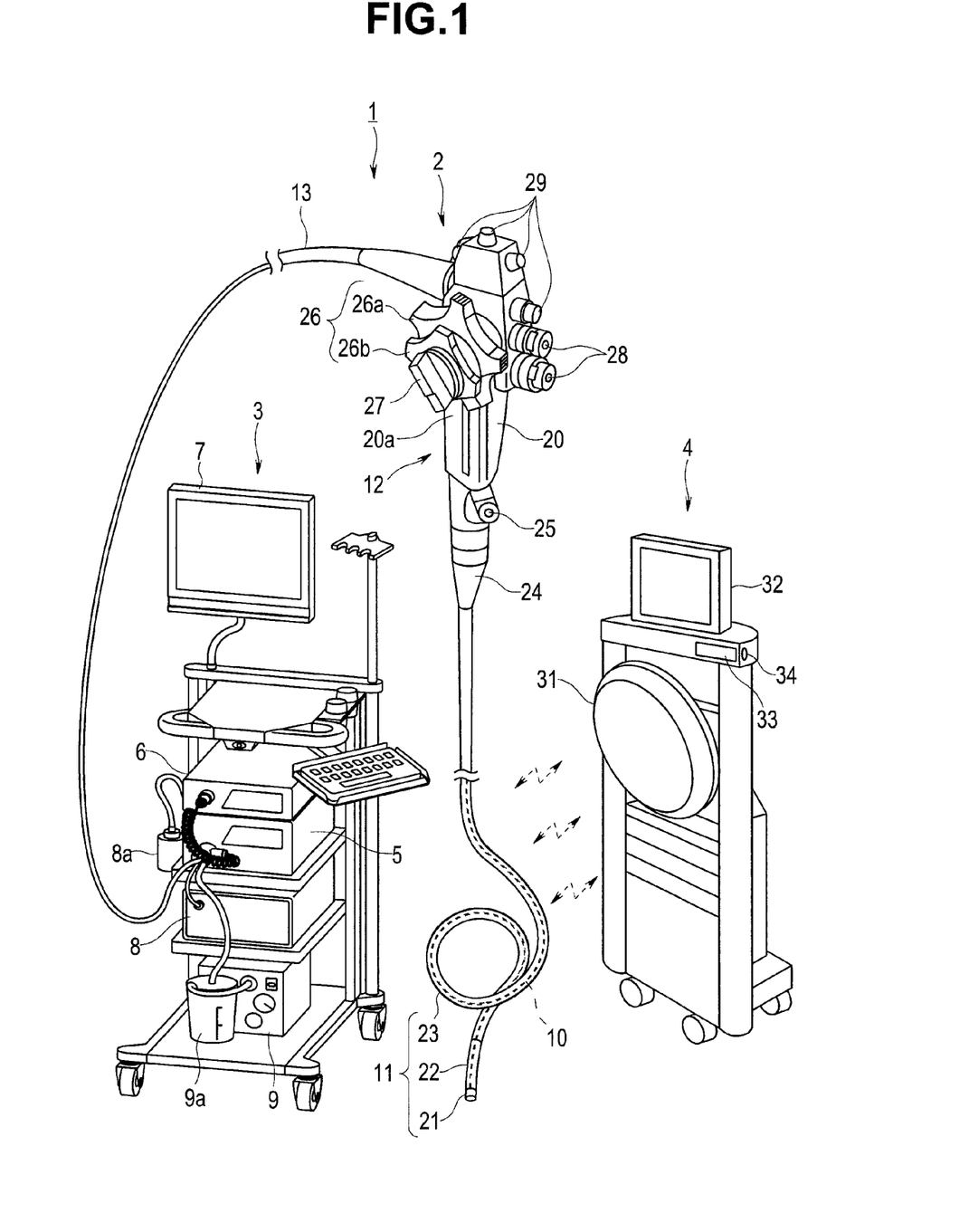
FIG. 1 is an overall configurational view showing an endoscope system according to one aspect of the present invention.
Figure 2:
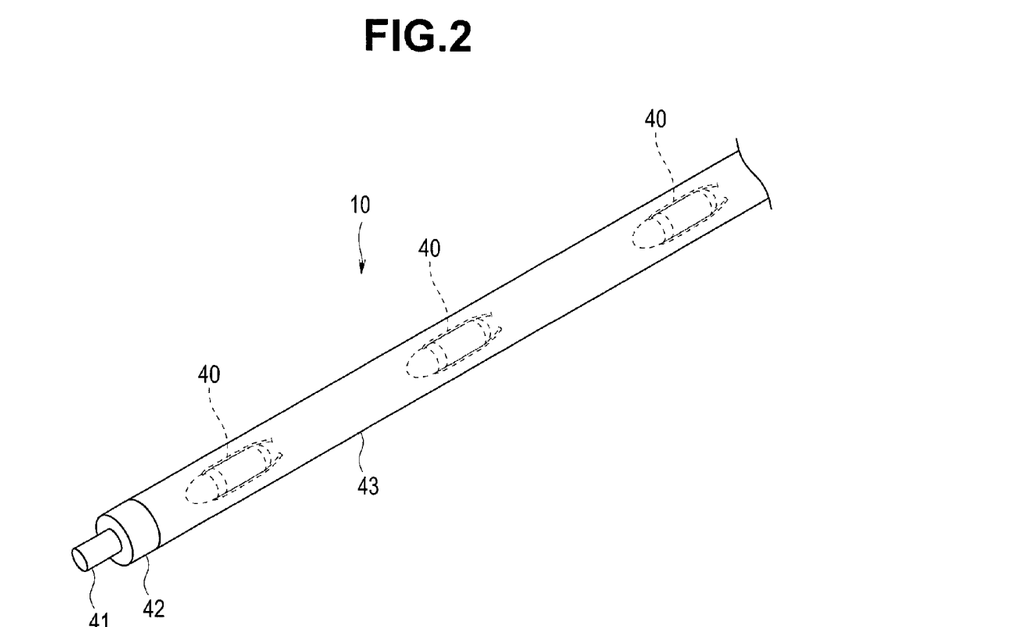
FIG. 2 is a perspective view showing a distal end side of an endoscope insertion shape observation probe and describing a configuration thereof.
Figure 3:
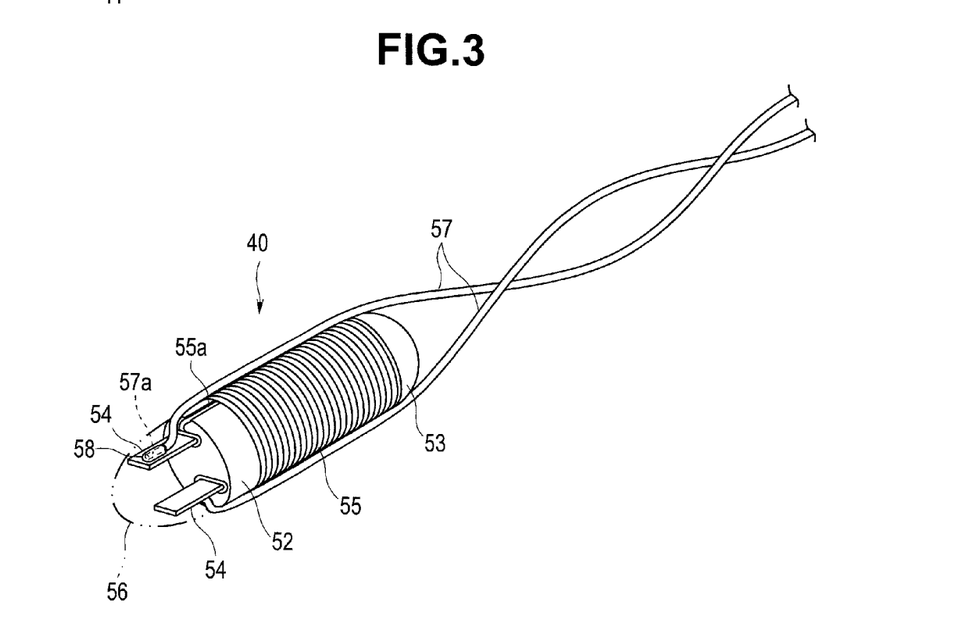
FIG. 3 is a perspective view showing a configuration of a magnetic coil connected to lead wires.
Figure 4:
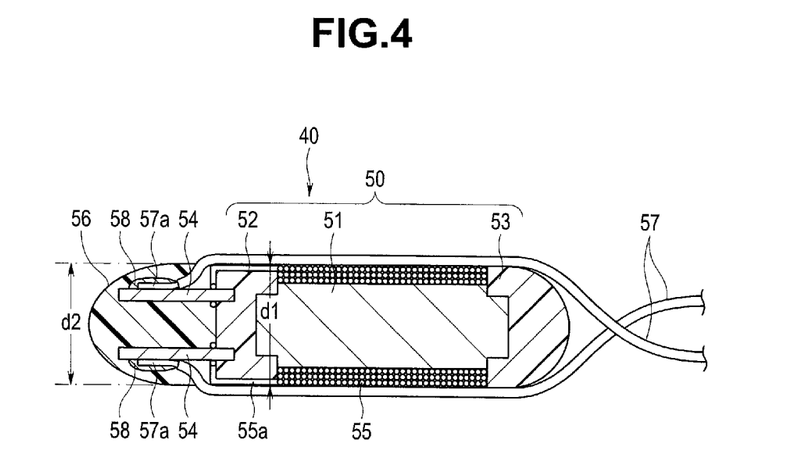
FIG. 4 is a cross-sectional view showing the configuration of the magnetic coil connected to the lead wires.
Figure 5:
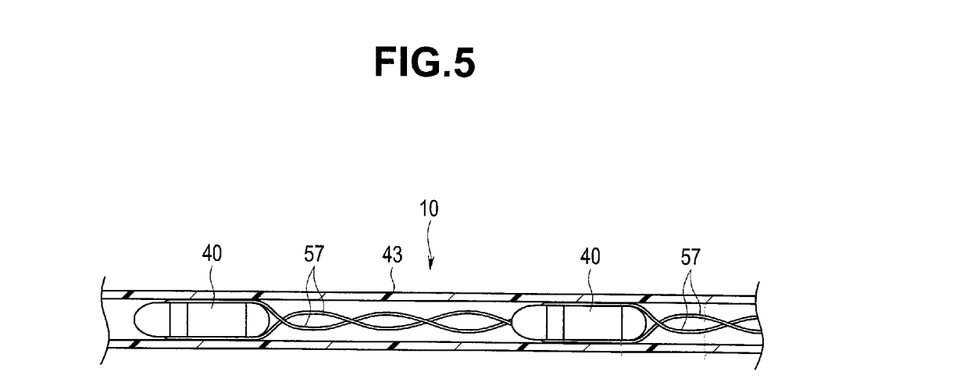
FIG. 5 is a partial cross-sectional view of the endoscope insertion shape observation probe.
Figure 6:
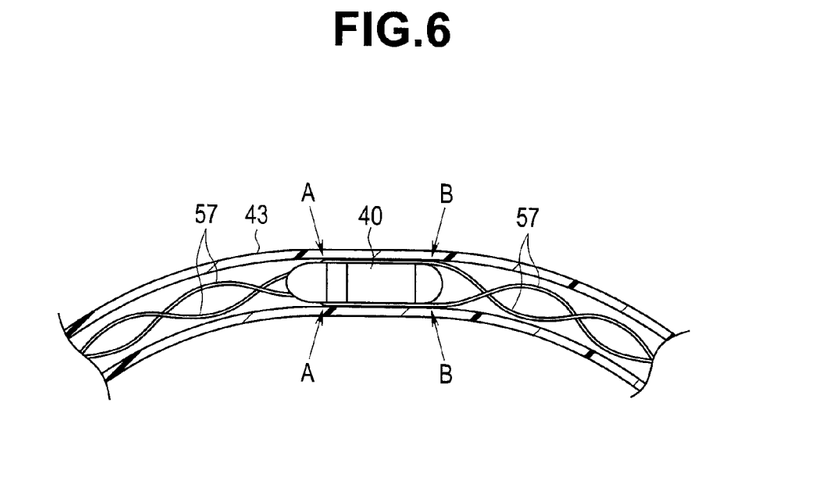
FIG. 6 is a partial cross-sectional view of the endoscope insertion shape observation probe in a bent state.
Figure 7:
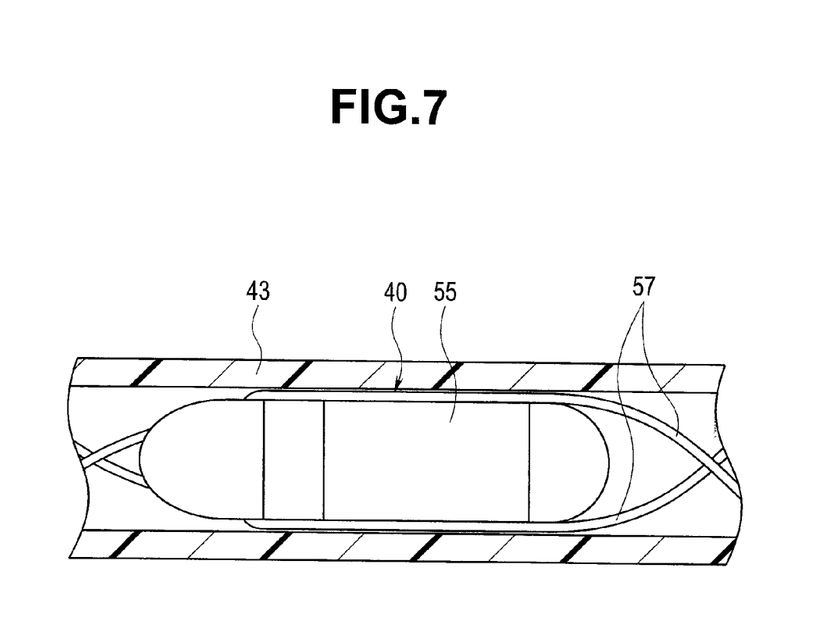
FIG. 7 is a partial cross-sectional view showing, in an enlarged manner, a part of the endoscope insertion shape observation probe where a magnetic coil is arranged.
Figure 8:
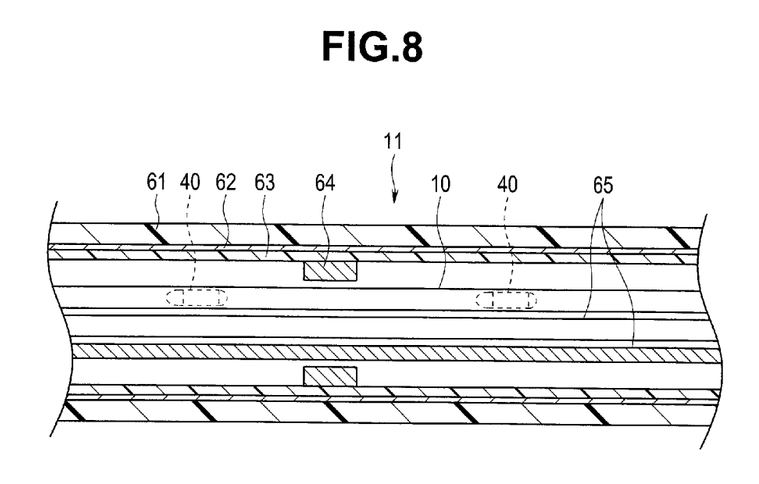
FIG. 8 is a partial cross-sectional view of an insertion portion of an endoscope in which the endoscope insertion shape observation probe is disposed.
Figure 9:
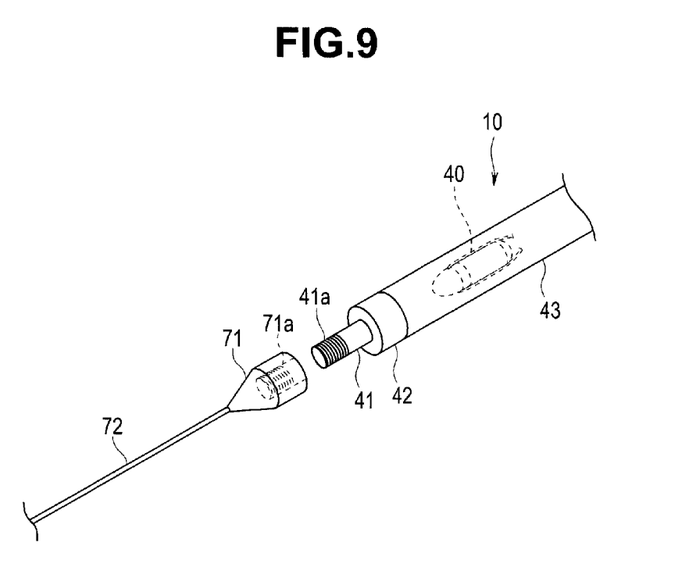
FIG. 9 shows a modified example of the endoscope insertion shape observation probe, and is a perspective view illustrating a distal end part of the endoscope insertion shape observation probe and a tension tool connected to a gut.
Figure 10:
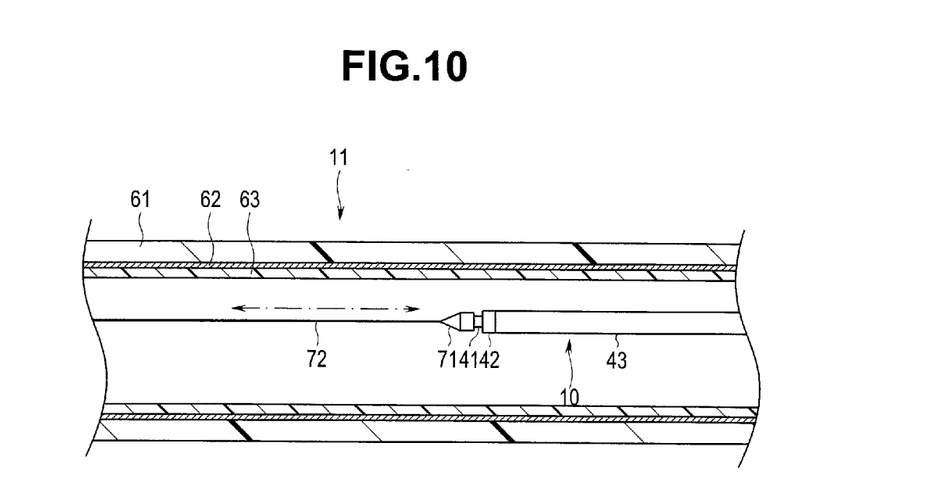
FIG. 10 is a cross-sectional view for describing a state where the endoscope insertion shape observation probe is inserted into the insertion portion of the endoscope using the tension tool.
Figure 11:
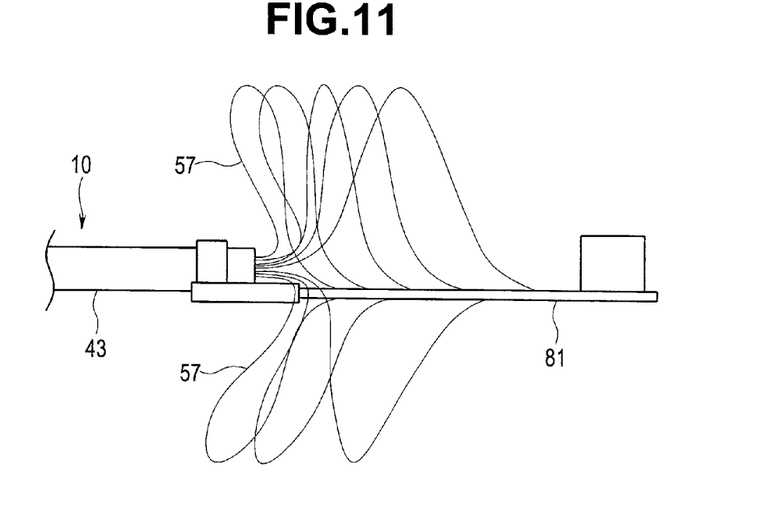
FIG. 11 illustrates a proximal end part of the endoscope insertion shape observation probe.
Figure 12:
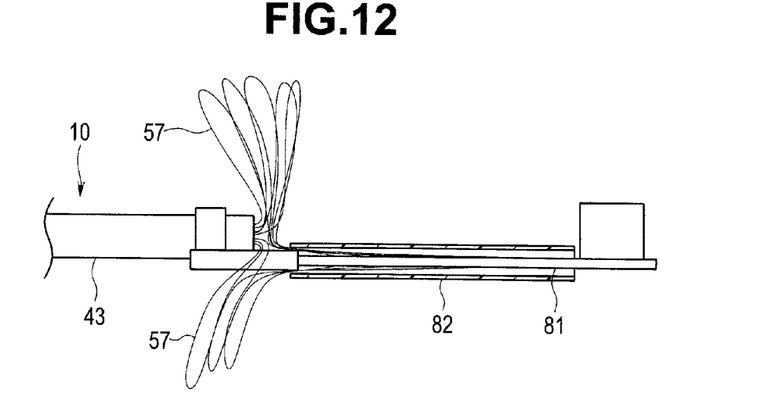
FIG. 12 illustrates a state where first fixing means is provided to the proximal end part of the endoscope insertion shape observation probe.
Figure 13:
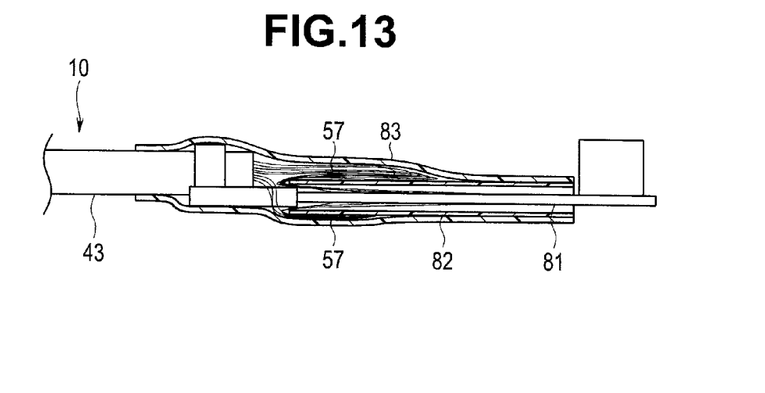
FIG. 13 illustrates a state where second fixing means is provided to the proximal end part of the endoscope insertion shape observation probe.

First, one embodiment of the present invention will be described with reference to the drawings FIG. 1 to FIG. 13. FIG. 1 is an overall configurational view showing an endoscope system, FIG. 2 is a perspective view showing a distal end side of an endoscope insertion shape observation probe and describing a configuration thereof, FIG. 3 is a perspective view showing a configuration of a magnetic coil connected to lead wires, FIG. 4 is a cross-sectional view showing the configuration of the magnetic coil connected to the lead wires, FIG. 5 is a partial cross-sectional view of the endoscope insertion shape observation probe, FIG. 6 is a partial cross-sectional view of the endoscope insertion shape observation probe in a bent state, FIG. 7 is a partial cross-sectional view showing, in an enlarged manner, a part of the endoscope insertion shape observation probe where a magnetic coil is arranged, FIG. 8 is a partial cross-sectional view of an insertion portion of an endoscope in which the endoscope insertion shape observation probe is disposed, FIG. 9 shows a modified example, and is a perspective view illustrating a distal end part of the endoscope insertion shape observation probe and a tension tool connected to a gut, FIG. 10 is a cross-sectional view for describing a state where the endoscope insertion shape observation probe is inserted into an insertion portion of the endoscope using the tension tool, FIG. 11 illustrates a proximal end part of the endoscope insertion shape observation probe, FIG. 12 illustrates a state where first fixing means is provided to the proximal end part of the endoscope insertion shape observation probe, and FIG. 13 illustrates a state where second fixing means is provided to the proximal end part of the endoscope insertion shape observation probe.

Hereinafter, description will be made on an endoscope system 1 according to the present embodiment. Note that description is made supposing that the endoscope insertion shape observation probe according to the present invention is configured to be disposed in the insertion portion of the endoscope. However, the endoscope insertion shape observation probe may be directly connected to the endoscope insertion shape observation apparatus and configured to be insertable into a treatment instrument channel disposed in the insertion portion of the endoscope.

As shown in FIG. 1, the endoscope system 1 is configured by mainly including: an endoscope 2, a work trolley 3 on which instruments and the like connected to the endoscope are placed; and an endoscope insertion shape observation apparatus 4 which three-dimensionally displays a shape of an insertion portion 11 of the endoscope 2 on a monitor.

The endoscope 2 is configured by including the insertion portion 11 as an elongated hollow long member to be inserted into an observation target site, an operation portion 12 provided in a linked manner to a proximal end portion of the insertion portion 11, and a universal cable 13 extended from a side surface of the operation portion 12.

The insertion portion 11 has on a distal end side thereof a distal end portion 21, and a bending portion 22 as a bendable movable portion is connected at a rear portion of the distal end portion 21. Furthermore, a long flexible tube portion 23 which is made of a soft tubular member and has flexibility is provided in a linked manner at a rear portion of the bending portion 22. Note that an endoscope insertion shape observation probe 10 is incorporated in the insertion portion 11 along the longitudinal direction thereof.

The operation portion 12 is configured by including: an operation portion main body 20 which constitutes an operation grasping portion; a bend preventing portion 24 connected to the proximal end side of the flexible tube portion 23 of the insertion portion 11; and a treatment instrument insertion port 25 which is disposed in the vicinity of the bend preventing portion 24 and which serves as an opening portion of the insertion channel in the insertion portion 11.

A bending operation knob 26 for performing bending operation of the bending portion 22 of the insertion portion 11 is rotatably disposed on a surface 20a of the operation portion main body 20, and also switches 28, 29 for various endoscope functions are provided on the surface 20a. Note that an bending operation knob (angle knob) 26 includes a UD bending operation knob (UD angle knob) 26a for bending and operating the bending portion 22 in UD (UP/DOWN) direction, and an RL bending operation knob (RL angle knob) 26b for bending and operating the bending portion 22 in RL (RIGHT/LEFT) direction, and these knobs are disposed so as to overlap each other. In addition, an RL release knob 27b which is operated to stop/release the rotation of the RL bending operation knob 26b is provided at the center portion of the RL bending operation knob 26b. Note that also an UP release knob, not shown in FIG. 1, which is operated to stop/release the rotation of the UP bending operation knob 26b is also provided.

External devices such as a light source device 5, a video processor 6 as a CCU (camera control unit), a monitor 7, a compressor 8 to which a water-feeding tank 8a is connected via a tube, and a suction device 9 are placed on the work trolley 3. The light source connector provided at the extending end portion of the universal cable 13 of the endoscope 2 is detachably connected to the light source device 5. An electric connector extended from the light source connector is detachably connected to the video processor 6.

The light source device 5 supplies illumination light to a light guide, not shown, provided in the endoscope 2. That is, the light guide, to be described later, is disposed inside the universal cable 13, the operation portion 12, and the insertion portion 11 of the endoscope 2 according to the present embodiment, and the light source device 5 supplies, via the light guide, illumination light to an illumination optical system, to be described later, which constitutes an illumination window of the distal end portion 21. The illumination light is emitted by the illumination optical system to illuminate a region to be examined.

The video processor 6 converts image data obtained by picking up an image by image pickup means of the endoscope 2 into a video signal, and causes the monitor 7 to display the video signal. Furthermore, the video processor 6 receives operation signals from the switches 29 disposed at the operation portion 12 of the endoscope 2.

Based on the operation signals from the switches 29, the light source device 5 is controlled via the endoscope 2, and the compressor 8 or the suction device 9 is driven. The compressor 8 performs air/water feeding control for sending air to the water feeding tank 8a, to thereby feed air or water, normal saline, etc., as cleaning water in the water feeding tank to the distal end portion 21, via an air/water feeding channel of the insertion portion 11.

Furthermore, the suction device 9 is configured to suck substances such as filth, mucosa, blood, and the like from inside the body on the basis of the operation signal from the endoscope 2, and is connected to a tank 9a in which the sucked substances are collected. Note that the switches 28 are mechanical switches operated by a user at the time of feeding air or water.

The endoscope insertion shape observation apparatus 4 includes a substantially disk-shaped coil unit 31 which receives magnetism from magnetic coil units 40 provided in the endoscope insertion shape observation probe 10 in the insertion portion 11, and a liquid crystal monitor 32 for displaying the shape of the insertion portion 11. The endoscope insertion shape observation apparatus 4 includes an operation panel 33 on an upper front surface of a frame, and on the side surface of the frame in the vicinity of the upper front surface, a scope/probe connector 34 is provided. Note that the scope/probe connector 34 can be directly connected with the endoscope insertion shape observation probe 10 of a type configured to be inserted into the treatment instrument channel in the endoscope 2 or insertion portion 11.

Hereinafter, detailed description will be made on the endoscope insertion shape observation probe 10 according to the present embodiment.

As shown in FIG. 2, the endoscope insertion shape observation probe 10 is configured by including a distal end ferrule 42 to which a distal end pin 41 is provided, a heat-shrinkable tube 43 connected to the distal end ferrule 42, and a plurality of magnetic coil units 40 disposed in the heat-shrinkable tube 43 at equal intervals. Note that the plurality of magnetic coil units 40 are disposed in the heat-shrinkable tube 43 at equal intervals by the separation distance between the respective magnetic coil units being specified by a wire rod (not shown) bonded to the side surface at the time of manufacturing.

As described above, the endoscope insertion shape observation probe 10 is disposed in the insertion portion 11 of the endoscope 2 in the longitudinal direction of the insertion portion 11. Note that the distal end pin 41 is inserted and fixed to the distal end portion 21 of the endoscope 2, though not shown.

As shown in FIG. 3 and FIG. 4, the magnetic coil unit 40 includes a bobbin 50 composed of a core 51 as a cylindrical magnetic core made of iron, ferrite, or the like, a distal end cap 52 of a front side outward flange, which is fitted to the distal end of the core 51 and made of a substantially cylindrical insulation body, and a proximal end cap 53 of a rear side outward flange, which is fitted to the proximal end of the core 51 and made of a spherical cap-shaped insulation body. The core 51 of the bobbin 50 includes a coil portion 55 formed by winding a copper wire 55a in a circumferential direction by a predetermined number of times.

Two terminal portions 54 are formed such that wires 57a of a pair of twined lead wires 57 as signal lines are electrically connected, by brazing portions 58 such as soldering, respectively on surfaces of the two terminal portions, which are directed outward sides of the magnetic coil unit 40. That is, the two terminal portions 54 have plate faces parallel to each other, and the respective wires 57a of the lead wires 57 are electrically connected to the surface sides which are directed in opposite directions away from each other toward outward sides of the magnetic coil unit 40, by the brazing portions 58. In this state, the distal end parts of the lead wires 57 are not bent at a sharp angle, and the wires 57a are brazed to the terminal portions 54, respectively. Note that the configuration of the lead wires 57 is not limited to a pair of wires 57a.

In addition, on the front side of the distal end cap 52, a protective member 56 such as adhesive is placed so as to have a distal end ammunition shape, spherical cap shape, etc., for covering the two terminal portions 54 to which the wires 57a are connected, respectively. Note that the protective member 56 is formed such that a dimension of a diameter (outer diameter d2) perpendicular to a longitudinal axis in an anteroposterior direction of the magnetic coil unit 40 is equal to or smaller than the outer diameter d1 of the magnetic coil unit 40 ($d1 \geq d2$).

The plurality of magnetic coil units 40 are inserted and placed in the heat-shrinkable tube 43 at equal intervals. Note that, since the distal ends of the magnetic coil units are formed in the distal end ammunition shape, spherical cap shape, etc., when the plurality of magnetic coil units 40 are inserted and placed in the heat-shrinkable tube 43, the magnetic coil units can be smoothly inserted without getting stuck in the heat-shrinkable tube 43.

Then, the distal end pin is connected to the distal end of the heat-shrinkable tube 43, and heat is applied to the heat-shrinkable tube 43, thereby enabling the magnetic coil units to be held. That is, the plurality of magnetic coil units 40 contact the inner surface of the heat-shrinkable tube 43 to be held thereby due to heat shrinkage of the heat-shrinkable tube 43.

Note that the heat-shrinkable tube 43 does not shrink to the extent that the shrunk inner diameter of the tube becomes smaller than the outer diameter of each of the magnetic coil units 40, and the lead wires 57 on the magnetic coil units 40, which extend from the front side of the magnetic coil units 40, are placed sandwiched between the heat-shrinkable tube 43 and the magnetic coil units 40.

The endoscope insertion shape observation probe 10 is thus completed (see FIG. 2 and FIG. 5). The endoscope insertion shape observation probe 10 is, as described above, inserted into the insertion portion 11 of the endoscope 2, and incorporated in the insertion portion 11 with the distal end pin 41 fixed to the distal end portion 21 of the endoscope 2.

The endoscope insertion shape observation probe 10 thus configured is changed to be a bent or bowed shape according to the bending shape (bowed shape) of the insertion portion 11 (see FIG. 6). In particular, the bent or bowed shape of the endoscope insertion shape observation probe 10 is the steepest inside the bending portion 22 of the insertion portion 11.

Thus, in the endoscope insertion shape observation probe 10 changed to be a bent or bowed shape according to the bending shape of the insertion portion 11, the lead wires 57 sandwiched between the heat-shrinkable tube 43 and the magnetic coil unit 40 and extended rearward are in a state held by the inner surface of the heat-shrinkable tube 43 covering the base parts (parts indicated by the arrows A in FIG. 6) of the lead wires, which are led from the protective member 56 of the magnetic coil unit 40. As a result, the lead wires 57 are not likely to be bent, and the load is hard to be applied to the lead wires 57.

In other words, in the endoscope insertion shape observation probe 10, the lead wires 57 are connected at the front side of each of the magnetic coil units 40 to be extended rearward along the outer circumferential portion of each of the magnetic coil units 40, and the heat-shrinkable tube 43 covers and holds the base parts (the parts indicated by the arrows A in FIG. 6) of the lead wires 57 which are led from the protective member 56. As a result, the base parts of the lead wires 57 extended from the protective member 56 are prevented from moving, and the load is hard to be applied to the lead wires 57.

That is, as shown in FIG. 7, the lead wires 57 are sandwiched between the side peripheral part of the coil portion 55 of the magnetic coil unit 40 and the inner circumferential surface of the heat-shrinkable tube 43, thereby preventing the lead wires 57, which extend with the wires 57a connected to the terminal portions 54 (see FIG. 3 and FIG. 4) by the brazing portions 58, from bending at a sharp angle. In other words, the lead wires 57 are sandwiched between the coil portion 55 of the magnetic coil unit 40 and the inner circumferential surface of the heat-shrinkable tube 43, and the respective wires 57a connected to the terminal portions 54 by the brazing portions 58 are prevented from bending at a sharp angle on the boundary surfaces of the terminal portions 54. As a result, load is hard to be applied to the lead wires.

Furthermore, the lead wires 57 are twined in a space of the heat-shrinkable tube 43, and the portions of the lead wires located at the rear parts (parts indicated by the arrows B in FIG. 6) of the magnetic coil unit 40 can move freely to some extent. Therefore, the lead wires 57 are hardly subjected to the load caused by tension generated by bending. In addition, since the proximal end cap 53 of the magnetic coil unit 40 is in a spherical cap shape, the lead wires 57 do not bend at a sharp angle toward the space of the heat-shrinkable tube 43. As a result, load is hard to be applied to the lead wires.

The endoscope insertion shape observation probe 10 has such a configuration as to reduce the load to be applied to the sites where the lead wires 57 are likely to be disconnected due to the change in shape by bending or bowing. Note that, as result of performing a bend test repeatedly on the endoscope insertion shape observation probe 10 according to the present embodiment under a predetermined condition, the bend test which causes disconnection of the lead wires 57 in the conventional configuration can be performed on the endoscope insertion shape observation probe according to the present embodiment more than twice the number of times, compared with a conventional configuration under the same condition, thereby capable of providing a configuration in which the resistance of the endoscope insertion shape observation probe has remarkably increased.

As described above, the endoscope insertion shape observation probe 10 according to the present embodiment is capable of preventing disconnection of the lead wires connected to the plurality of magnetic coils and improving the resistance property of lead wires without increasing the outer diameter of the lead wires.

Incidentally, the endoscope insertion shape observation probe 10 contacts and interferes with other components disposed in the insertion portion 11 of the endoscope 2. Therefore, according to the bending shape (bowed shape) of the insertion portion 11, there is a possibility that the lead wires 57 are compressed on each of the magnetic coil units 40 to be disconnected.

Therefore, as shown in FIG. 8, the endoscope insertion shape observation probe 10 can reduce the possibility of the disconnection of the lead wires 57 due to compression by arranging the magnetic coil units 40 at a part where the filling rate of the internal components 65 as other components such as various channels, cables, bending operation wires, and light guide bundles is small in the insertion portion 11.

Specifically, in the insertion portion 11 of the endoscope 2, the flexible tube portion 23 is constituted of an outer cover 61, a braid 62, and a flexible tube 63, and the bending portion 22 is provided with bending pieces instead of the flexible tube 63. If holding portions 64 for holding other internal components 65, for example, the bending operation wires are provided so as to protrude in the inner diameter direction of the flexible tube 63, the internal space where the holding portions are provided becomes narrow.

Therefore, the filling rate of other internal components 65 in the insertion portion 11 becomes large. If the magnetic coils 40 are not disposed at the region where the filling rate is large, the interference between other internal components 65 and the lead wires 57 is prevented and the lead wires 57 are not compressed. As a result, occurrence of disconnection of the lead wires 57 can be avoided as much as possible.

Note that, in the bending portion 22, the internal space becomes narrow at the connecting portion between the respective bending pieces and at the joint portion between the proximal-most bending piece and the flexible tube. Therefore, it is preferable not to arrange the magnetic coil units 40 at such portions.

In addition, when failure occurs in the endoscope insertion shape observation probe 10 provided in the insertion portion 11 of the endoscope 2 due to disconnection of the lead wires 57, etc., and there is a need for repair, in order to reduce the repair cost, as an exchange method of the probe, a method of directly winding the gut on the distal end pin 41, what is called, a ropeway method has been conventionally employed. In the insertion portion 11 of the recent endoscope 2 in which the filling rate of the various components has increased, when the repaired endoscope insertion shape observation probe 10 or a new endoscope insertion shape observation probe 10 is drawn into the insertion portion 11, there is a possibility that the distal end pin 41 gets stuck in the insertion portion 11 and the probe cannot be exchanged, or the stuck distal end pin causes damages on the inside the insertion portion 11 and other internal components, and the insertion portion 11 itself or other internal components themselves have to be exchanged, which might lead to an expensive repair cost.

Therefore, as shown in FIG. 9, the endoscope insertion shape observation probe 10 includes a screw groove 41a formed at the distal end pin 41. In order to facilitate the exchange of the endoscope insertion shape observation probe 10 in the insertion portion 11, it is preferable to use an instrument including a tension tool 71 which has a screw groove 71a formed in accordance with the screw groove 41a so as to screwable to the distal end pin 41 and which is connected with a gut 72. Note that the tension tool 71 is formed in a tip-tapered shape and the gut 72 is connected to the distal end center thereof.

If such an instrument is used, the repaired endoscope insertion shape observation probe 10 or a brand-new endoscope insertion shape observation probe 10 becomes linear in the pulling direction of the gut 72 by the tension tool 71 connected to the distal end pin 41, thereby enabling the endoscope insertion shape observation probe 10 to be smoothly inserted into the insertion portion 11 without causing damages on the inside of the insertion portion 11 and other internal components.

Incidentally, in the endoscope insertion shape observation probe 10, the respective lead wires 57 have extra length for repair, for the purpose of restoring erroneous brazing operation such as soldering of the respective lead wires 57. In the conventional endoscope insertion shape observation probe 10, a method has been used in which the length of the heat-shrinkable tube 43 is increased in accordance with the extra length of the lead wires 57, and the extra length is wound and accommodated in the endoscope 2. However, in the endoscope 2 having a small internal space, it is difficult to ensure the accommodation space for the extra length, which has made the assembly of the endoscope 2 complicated.

Therefore, as shown in FIGS. 11 to 13, the respective lead wires 57 which have repair length are bundled on a terminated substrate 81, and held by a first fixing member 82 such as a tube, a tape, an adhesive, or the like, with the repair length being left. Then, the repair length parts of the respective lead wires 57, which are not held by the first fixing member 82, are put together into two on and under the substrate 81 and folded so as to overlap the first fixing member 82, and held by the second fixing member 83 such as a tube, a tape, an adhesive, or the like. According to such a configuration, the repair length parts of the respective lead wires 57 of the endoscope insertion shape observation probe 10 can be compactly accommodated on the substrate 81.

The invention described in the above embodiment is not limited to the contents described in the above embodiment but various modifications thereof are possible without departing from the gist of the invention in a practical stage. Furthermore, the above-described embodiment includes inventions of various stages, and by combining a plurality of constituent components disclosed in the embodiment, inventions of various stages can also be extracted.

For example, even if some constituent components are deleted from all the constituent components shown in the above-described embodiment, if the problem to be solved by the invention can be solved and the effects of the invention can be obtained, the configuration in which some constituent components are deleted can be extracted as an invention.

What is claimed is:

1. An endoscope insertion shape observation probe including a plurality of magnetic coil units disposed in a tube, comprising:
    a bobbin including a first insulation member provided at a front end of a core made of a magnetic member and a second insulation member provided at a rear end of the core;
    a coil portion formed by winding metal lines on the core;
    at least two terminal portions to which the metal lines are electrically connected; and
    signal lines, wires of which are electrically connected to the terminal portions, the signal lines being extended rearward while being sandwiched between an inner circumferential surface of the tube and an outer circumferential portion of the coil portion,
    wherein the at least two terminal portions are formed such that the wires are brazed respectively on surface sides of the respective terminal portions, the surface sides being directed in opposite directions away from each other toward outward of each of the plurality of magnetic coil units.

2. The endoscope insertion shape observation probe according to claim 1, wherein a rear side end portion of the coil portion is formed in a spherical cap shape.

3. The endoscope insertion shape observation probe according to claim 1, further comprising an insulation protective member disposed at a front side of the first insulation member, so as to cover the terminal portions.

4. The endoscope insertion shape observation probe according to claim 3, wherein the protective member is formed such that a dimension of a diameter perpendicular to an axis in an anteroposterior direction of each of the magnetic coil units is smaller than a dimension of an outer diameter of each of the magnetic coil units.

5. The endoscope insertion shape observation probe according to claim 3, wherein the protective member is formed in a distal end ammunition shape or in a spherical cap shape.

6. The endoscope insertion shape observation probe according to claim 1, wherein the second insulation member is formed in a spherical cap shape.

7. The endoscope insertion shape observation probe according to claim 1, wherein the at least two terminal portions have plate faces which are parallel to each other.

* * * * *